US010131727B2

(12) United States Patent
Singh et al.

(10) Patent No.: US 10,131,727 B2
(45) Date of Patent: Nov. 20, 2018

(54) SOLID STATE MATRIX, PROCESS OF PREPARATION THEREOF, AND PROCESS OF PREPARATION OF THEAFLAVINS

(75) Inventors: Harsh Pratap Singh, Himachal Pradesh (IN); Kapil Sharma, Himachal Pradesh (IN)

(73) Assignee: COUNCIL OF SCIENTIFIC AND INDUSTRIAL RESEARCH, New Dehli (IN)

( * ) Notice: Subject to any disclaimer, the term of this patent is extended or adjusted under 35 U.S.C. 154(b) by 2010 days.

(21) Appl. No.: 12/225,793

(22) PCT Filed: Mar. 21, 2007

(86) PCT No.: PCT/IB2007/000699
§ 371 (c)(1),
(2), (4) Date: Jul. 24, 2009

(87) PCT Pub. No.: WO2007/116259
PCT Pub. Date: Oct. 18, 2007

(65) Prior Publication Data
US 2009/0298140 A1    Dec. 3, 2009

(30) Foreign Application Priority Data
Mar. 31, 2006   (IN) .............................. 929/DEL/2006

(51) Int. Cl.
| | |
|---|---|
| *C12P 17/16* | (2006.01) |
| *C12N 9/04* | (2006.01) |
| *C07H 21/04* | (2006.01) |
| *C08F 220/18* | (2006.01) |
| *C08F 8/30* | (2006.01) |
| *C12N 11/08* | (2006.01) |
| *C12P 17/06* | (2006.01) |

(52) U.S. Cl.
CPC .............. *C08F 220/18* (2013.01); *C08F 8/30* (2013.01); *C12N 11/08* (2013.01); *C12P 17/06* (2013.01)

(58) Field of Classification Search
CPC ...... C12N 11/08; C12N 9/0059; C12N 11/04; C12N 11/14; C12N 9/0004; C12N 11/02; C12P 13/225; C12P 17/00; C12Q 1/005; C12Q 1/001; C12Q 1/26; C12Y 110/03001

See application file for complete search history.

(56) References Cited

U.S. PATENT DOCUMENTS

| | | | |
|---|---|---|---|
| 6,096,359 A | 8/2000 | Bombardelli et al. | |
| 6,113,965 A | 9/2000 | Goodsall et al. | |
| 6,383,392 B1 | 5/2002 | Bonrath et al. | |
| 6,531,162 B1 | 3/2003 | Llewellyn | |
| 2004/0097430 A1* | 5/2004 | Zhao et al. ..................... | 514/27 |
| 2004/0097432 A1 | 5/2004 | Rob-Schmidt et al. | |

FOREIGN PATENT DOCUMENTS

EP    0891973 B1    1/1999

OTHER PUBLICATIONS

Hilhong Bao, Master Thesis, McGill University, May 1999, p. 1-84.*
Jiang et al. Role of anthocyanins, polyphenol oxidase and phenols in lychee pericarp browning, J of the Science of Food and Agriculture, (2000), 80: 305-310.*
Duran et al. Applications of laccases and tyrosinases (phenoloxidases) immobilized on different supports: a review, Enzyme and Microbial Technology, vol. 31, Issue 7, Dec. 2, 2002, pp. 907-931.*
X. Huaiguo et al., "A highly stable biosensor for phenols prepared by immobilizing polyphenol oxidase into polyaniline-polyacrylonitrile composite matrix", Database Compendex [online], Engineering Information, Inc., New York, NY XP002455229, abstract & TALANTA May 16, 2002, pp. 289-295.
A. Cirpan et al., "Immobilization of invertase in conducting copolymers of 3-methylthienyl methacrylate", Bioelectrochemistry, 59 (2003) 29-33.

(Continued)

*Primary Examiner* — Iqbal H Chowdhury
(74) *Attorney, Agent, or Firm* — Clark & Brody

(57) ABSTRACT

The present invention relates to a process for the development of a highly efficient solid state matrix by the activation of acrylate based polymer resin having specialized functional groups with 1,1-Carboxyl diimidazole for immobilizing biologically active macromeloecules such as oxidases, in particular plant oxidases and the most preferred being tea polyphenol oxidase through indirect covalent bonding/cross linking on such activated polymer resin support, are thermally stable, gives very high number of turnovers in vitro ("n" times) with tea substrate forming exclusive product Theaflavins without any loss of biological activity and leaving the product remaining in vitro with adherence to matrix rendering the matrix safe towards product poisoning and subsequent partial or complete loss of biological activity of the matrix bound enzyme system and thus well adapted to and well suited biorectors based on such systems. It is unique with respect to its recyclability or otherwise uneconimical tea substrates such as seed and flower substrates into theaflavins both with respect to crude substrate or purified ones.

8 Claims, 4 Drawing Sheets

(56) References Cited

OTHER PUBLICATIONS

Figure 1:
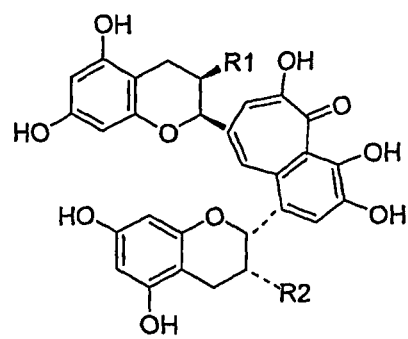
Figure 1:
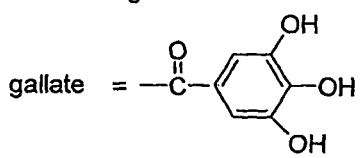

A. Abuchowski et al., "Effect of Covalent Attachment of Polyethylene Glycol on Immunogenicity and Circulating Life of Bovine Liver Catalase", The Journal of Biological Chemistry, vol. 252, No. 11, Jun. 10, 1977, pp. 3582-3586.
N. Katre et al., "Chemical modification of recombinant interleukin 2 by polyethylene glycol increases its potency in the murine Meth A sarcoma model", Proc. Natl. Acad. Sci. USA, vol. 84, pp. 1487-1491, Mar. 1987.
M. Arica et al., "Immobilization of polyphenol oxidase on carboxymethylcellulose hydrogel beads: preparation and characterization", Polymer International 49, pp. 775-781, 2000.
N. Subramanian et al., "Role of Polyphenol Oxidase and Peroxidase in the Generation of Black Tea Theaflavins", J. Agric. Food Chem., 1999, 47, pp. 2571-2578.
F. Veronese et al., "Surface Modification of Proteins; Activation of Monomethoxy-Polyethylene Glycols by Phenylchloroformates and Modification of Ribonuclease and Superoxide Dismutase", Applied Biochemistry and Biotechnology, vol. 11, 1985, abstract.

\* cited by examiner

Theaflavin                      R1=OH, R2=OH
Theaflavin-3-monogallate     R1=OH, R2=gallate
Theaflavin-3'-monogallate    R2=OH, R1=gallate
Theaflavin-3,3'-digallate       R1= R2=gallate

SOLID STATE MATRIX, PROCESS OF PREPARATION THEREOF, AND PROCESS OF PREPARATION OF THEAFLAVINS

FIELD OF THE INVENTION

The present invention particularly relates to a solid state matrix, process of preparation thereof, and process of preparation of theaflavins.

More particularly, the present invention relates to a process for the development of a highly efficient solid state matrix for immobilizing plant oxidase enzyme both of soluble and bound forms especially tea polyphenol oxidase (EC 1.10.3.1) for continuous batch production and total conversion of tea substrates to theaflavins both from purified tea substrate as well as crude tea substrate preparations where the matrix always converts all of the substrates available to theaflavins and thus provides a means to make theaflavins (w/w) in direct proportion to substrates available in reaction medium.

BACKGROUND OF THE INVENTION

Theaflavins are a group of polyphenolic compounds having general structure as shown in table 2 and are formed by the enzyme mediated reaction of tea polyphenol oxidase (PPO) (EC 1.10.3.1), found native to tea leaves and in other organs of tea plant with tea catechins (flavan-3-ols and their gallated esters), as its substrate, during black tea manufacture. The substrates for the formation of this reaction are present in maximum amount in tender shoots of tea plant comprising apical two leaves and an attached bud and in lesser quantities in all parts of tea plant and so is the enzyme PPO. (Reference may be made to Wickremsinghe, R. L. and Perera, K. P. W. C. (1972), Journal of the National Science Council, Sri Lanka; 1, 111-21). (Reference may also be made to Wickremsinghe, R. L., Roberts. G. R. and Perera, B. P. M. (1967), Tea quarterly; 38, 309-10). The primary substrate compounds are derivatives of flavan-3-ols commonly known as catechins as shown in table 1. Reference may be made to Yaminishi, Tei (1990), Development in Food Science, 25, Russell L. Rouseff, Bitterness in Foods and Beverages, Elsevier London. Chapter 9 wherein it is stated to include (−) epicatechin (EC); (−) epigallocatechin (EGC) and their gallate esters. Small amounts of (+) catechin and (+) gallocatechin are also found.

Catechins may be as high as 30% in Assamica varieties and only around 10% in Sinensis varieties. Reference may be made to Sanderson G. W. (1972), In Structural and Functional Aspects of Phytochemistry Runecleles V. C. ed. Academic Press, New York., 271-280 wherein it is reported that in black tea, the amount of theaflavins formed are partly 0.3-1.8 percent of the dry weight of black tea and thearubigins which are heterogeneous group of compounds comprise about 9-19% of black tea leaf. Reference may also be made to various reviews on the subject published in the past wherein chemistry of tea and its constituents are discussed in details. The matrix bound tea polyphenol oxidase is unique in terms of its high reactivity towards tea substrates, repeated recyclability for 'n' number of times without losing any activity, non-adherance of formed product to matrix thus allaying fear of product poisoning of matrix bound enzyme system, enhanced thermal stability and total conversion of tea substrates to end product of theaflavins both from purified and non-purified tea substrates.

TABLE 1

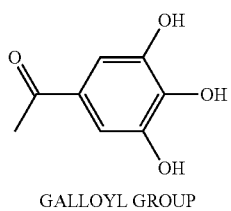

GALLOYL GROUP

| | R1 | R2 | M.W. |
|---|---|---|---|
| (−)-EPICATECHIN | H | H | 290 |
| (−)-EPIGALLOCATECHIN | OH | H | 306 |
| (−)-EPICATECHIN GALLATE | H | GALLOYL GROUP | 442 |
| (−)-EPIGALLOCATECHIN GALLATE | OH | GALLOYL GROUP | 456 |

TABLE 2

| | R1 | R2 | M.W. |
|---|---|---|---|
| THEAFLAVIN | H | H | 564 |
| THEAFLAVIN GALLATE-A | H | GALLOYL GROUP | 716 |
| THEAPLAVIN GAILATE-B | GALLOYL GROUP | H | 716 |
| THEAFLAVIN DI GALLATE | GALLOYL GROUP | GALLOYL GROUP | 868 |

The polyphenol oxidase immobilized on derivatised acrylate based polymer resin helps in the production of theaflavins from tea substrates. Theaflavins are a group of condensed catechins produced during the processing of black tea. (Reference may be made to Goodsall Chris W., Safford Dick (Sep. 1-30, 1998), Second International Electronic Conference on Synthetic Organic Chemistry (ECSOC-2). These are responsible for the brightness, briskness of tea infusions and have the same antioxidant properties of free catechins, having pleasing potential of being used as food colorants, anticancer substance and important neutraceuticals. (Reference may be made to Miller, N. J., Castelluccio, C; Tijburg, L., Rice-Evans, C. (Aug. 19, 1996), FEBS Lett,;

392(1).,40-41). Being a natural product they may also be used as a coating coloring substance for tablets NAD or as anti rancid compounds in oils and fats and in cosmetic preparations. Theaflavins prevent cellular DNA damage by inhibiting oxidative stress by suppressing cytochrome P450 IAI in cell cultures. (Reference may be made to Feng, Q., Torii, Y; Uchida, K; Nakamura, Y., Hara, Y; and Osawa, T. J. (Jan. 2, 2002), Agri Food Chem; 50(1); 213-216). Theaflavins also inhibit tumor growth and inflammation (Reference may be made to. Dass, M; Sur, P; Gomes, A; Vedasiromoni, J. R. and Ganguly D. K. (2002), Phytother. Res., 16, S40-S44).

In addition to this, theaflavins also possess anti-clastogenic and anti-mutagenic effect (Reference may be made to Gupta S, Chaudhuri T, Seth P, Ganguly D. K. and Giri A. K. (2002), Phytother. Res., 16, 655-661. However, theaflavins constitute only 1.5 to 2.5 percent (dry wt.) of the black tea even though the green leaf has upto 20 percent (dry wt.) catechins. (Reference may be made to Harold, N and Graham, P. D. (1992), Green tea composition, Consumption, and Polyphenol Chemistry. Preventive Med., 21, 334-350).

The enzyme polyphenol oxidase involved in generation of theaflavins present in tea shoots (Reference may be made to Bajaj, K. L., Anan, T; Tsushida, T & Ikegaya K. (1987), J. Agric. Biol. Chem., 51, 1767-1772). has been solubilised and immobilized on the above-mentioned matrix.

Further improvements offered by the invention include the ability to maximize the biological activity retention and/or to increase the activity of target molecules, minimize the toxicity of product, minimize the reaction time at physiological pH, reduces contamination of the product and improves the stability of the activated polymer.

Limitations of other methods for immobilizing biologically active macromolecules are:
1. Long Coupling time
2. Unphysiological pH leading to target molecules inactivation
3. Products contamination with either activated or inactivated polymer.
4. Polymer species or co-product toxic.
5. Limited use in aqueous solutions.
6. Activated polymer construct unstable.
7. Substantial loss of biological activity frequently seen with the cyanuric chloride method (Reference may be made to Abuchowski et al (1977a), Journal of Biological Chemistry, 252, 3582-3586) and carbonyldiimidazole method (Reference may be made to Beauchamp et al (1983), Analytical Biochemistry, 131, 25-33) and occasionally with phenylchloroformate (Reference may be made to Veronese et al (1985), Appl. Biochem. Biotechnol., 11, 141-152) and succinimedyl active ester methods (Reference may be made to Shadle et al; Katre et al (1987), Proc. Natl. Acad. Sci. USA, 84, 1487-1491).
8. Many methods recommend long coupling time and/or unphysiological pH, thus rendering target moieties less active or inactive (e.g. the carbonyldiimidazole, cyanuric chloride, phenylchloroformate and some succinimidyl active ester methods).
9. Some methods are unsuitable for use in aqueous solution, thus limiting the target molecules to those, which will tolerate non-aqueous solutions, (e.g. organic sulfonylhalide method using trifluoromethanesulfonyl chloride (Reference may be made to Mosbach & Nilson; Delgado et al (1990) Biotechnology and Applied Biochemistry, 12, 119-128).
10. Many methods use activated polymer species and/or produce co-products which are toxic in a wide range of beverages and which are potentially toxic in vivo if not separated from the product (e.g. Phenylchloroformate, cyanuric chloride methods.)In the current invention it has been found that most of the previously described methods are unsuitable because of the high levels of the product binding during active enzyme: polymer adduct reaction with substrates, causing matrix poisoning and partial or complete loss of biological activity and for unrecoverable product from active matrix, making it unsuitable as a material for bioreactor or repeated use.

OBJECTS OF THE INVENTION

The main object of the present invention is to provide a solid state matrix, process of preparation thereof, for the preparation of theaflavins.

Another object of the present invention is to use solid state matrix for immobilizing tea polyphenol oxidase enzyme for continuous batch production and total conversion of tea substrates to theaflavins.

Another object of the present invention is to use acrylate based polymer resins as a source material after suitable derivatization for the introduction of specialized functional groups for immobilization of oxidases preferably plant oxidases and especially tea polyphenol oxidase (PPO).

Yet another object of the present invention is to prepare theaflavins from tea substrates in direct proportion and yield (w/w) to the amount of substrates available in raw material (leaf, flower seed of tea plant) in an economical way with the help of bioreactor based on immobilized tea polyphenol oxidase (PPO) system.

Yet another object of the present invention is to develop the matrix and the immobilized matrix bound enzyme system so as to make repeated products from the system so developed under in vitro conditions of the reaction without any adherence of the product so formed to the matrix system enabling repeated and unlimited use of matrix bound enzyme system without fear of losing product, product poisoning of matrix bound enzyme and impaired or complete loss of biological activity of the matrix bound enzyme system.

Still another object of the present invention is to utilize uneconomical waste material from tea plant such as tea seeds, tea flowers, and pruning litter for obtaining tea substrates and converting them to high valued theaflavins.

Still yet another object of the present invention is to utilize low valued tea crop during the flushing season for obtaining tea substrates and converting them to high valued theaflavins.

Still yet another object of the present invention is to solubilize enzyme polyphenol oxidase (PPO) from tea leaves and other parts of tea plants in an economical manner and in high yield for immobilization purposes.

Still yet another object of the present invention is to provide the matrix system, which may remain stable at the temperature around 60 deg. C.

Still yet another object of the present invention is that the matrix can be used for at least 50 times for converting tea substrate into theaflavins without loss of enzyme activity.

Still yet another object of the present invention is to provide a process wherein the coversion of tea substrate to theaflavins is around 90 percent.

BRIEF DESCRIPTION OF THE DRAWINGS (FIG. 1) comparative spectrophotometric analysis of theaflavins as extracted from black tea and as produced from the immobilized enzyme system.

(FIG. 2) representing the comparative spectrophotometric analysis of theaflavins as extracted from black tea and as produced from the immobilized enzyme system.

(FIGS. 3 & 4) shows the preferred product being theaflavins as identified by spectrophotometric and HPLC analysis and compared with reference standard (Sigma) which shows absorbance at 380 nm and at 460 nm.

SUMMARY OF THE PRESENT INVENTION

Accordingly the present invention provides a process for the development of a highly efficient solid state matrix for immobilizing tea polyphenol oxidase enzyme for continuous batch production and total conversion of tea substrates to theaflavins which comprises the preparation of CDI (1,1-carbonyldiimidazole) activated acrylate based polymer resin, the process involves the addition of 2.0 g 1,1-Carbonyl diimidazole (CDI) in 50-ml dichloromethane taken in a flat bottomed flask maintained at 4° C. in an ice-bath, after the addition of 1,1-Carbonyl diimidazole, 4.0 g polymer resin was added to above solution and the whole mixture was stirred at room temperature (20° C.) on magnetic stirrer for half an hour, the product so formed was filtered through Buchner funnel using Whatman filter paper No.2 , the CDI activated polymer resin then washed with 25 ml dichloromethane and dried under vacuum and kept in a fridge at 4° C. till further use.

The indirect covalent bonding of target molecules, being in our case the enzyme proteins polyphenol oxidase (EC 1.10.3.1) isolated and solubilized in aqueous form in highly active state and in >80% yield from the leaves and other parts like flower, seeds, bark etc. of tea plant *Camellia sinensis* (L(O). Kuntze), with the derivatized polymer moieties of the matrix in order to so modify and improve the biological properties of the immobilized enzyme so as to catalyze conversion of available substrate in vitro to preferentially and entirely make the product (Theaflavins), chemically identified as 1,8-bis(3,4-dihydro-3,5,7-trihydroxy-2H-1-benzo-pyra-2-yl)-3,4,6-trihydroxy-5H-benzo-cyclo-hepten-5-one and commonly known as theaflavins. The substrates for this reaction normally present in all parts of tea plant in varying concentrations and proportions were isolated for and used either as crude or purified preparations to obtain theaflavins, in direct proportion to the available substrate present in such preparations, as final product.

DETAILED DESCRIPTION OF THE PRESENT INVENTION

Accordingly the present invention provide solid state matrix of formula III

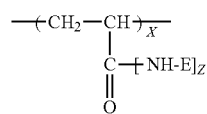

Formula III wherein X is up to about 30, Z is always one per carboxyl group in the polymer chain length, NH-E is polyphenol oxidase enzyme (PPO).

In an embodiment of the present invention, where the polyphenol oxidase used in the present invention is obtained from the plant selected from the group consisting of tea and litchi.

In an embodiment of the present invention, where the matrix is also stable at the temperature around 60 deg. C.

In an embodiment of the present invention, where the matrix is useful for the conversion of substrate selected from tea to the corresponding product theaflavins.

In an embodiment of the present invention, where the matrix can be used for at least 50 time to convert tea substrate into theaflavins without loss of enzyme activity.

In an embodiment of the present invention, where the polymer used is selected from a resin consisting of methylacrylate polymer, ethylacrylate polymer, propylacrylate polymer, butylacrylate polymer, preferably methylacrylate.

In an embodiment of the present invention, wherein the process for the preparation of solid state matrix of formula III

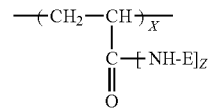

wherein X is upto about 30; The value of z is always one per carboxyl group in the polymer chain length, and NH-E is PPO, Comprising the steps of:
a). reacting the polymer of general formula Ia, wherein R is R may be —H, —CH$_3$, —C$_2$H$_5$, Y is up to about 30, X is up to about 30, or Ib, wherein R is R may be —H, —CH$_3$, —C$_2$H$_5$, Y is up to about 30, with 1,1-carbonyl-diimidazole at a temperature ranging between 4 deg C. to 20 deg C. for a period in the range between 30 minute to to 1 hr,

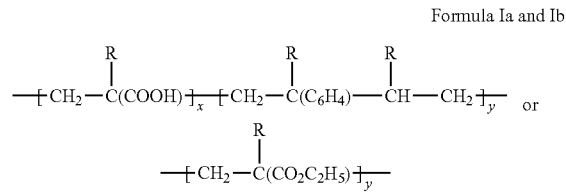

Formula Ia and Ib activated imidazole polymer of formula II

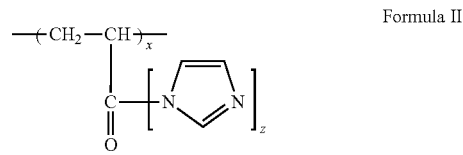

Formula II wherein x is up to about 30, the value of z is always one per carboxyl group in the polymer chain length,
b). filtering the product so formed in step (a) followed by washing with dichloromethane and drying to obtain activated acrylate resin,
c). reacting the activated polymer of formula IT with the target moiety selected from PPO preferably tea PPO, at a temperature range 4 deg. C. to 25 deg. C. for a period in the range between 1 hour to 2 hours in an aqueous phosphate buffer (pH 6.2) medium;
d). immobilizing the biologically active macromolecule on activated acrylate resin to obtain the desired matrix of formula III.

In an embodiment of the present invention, where the target moiety used is of PPO, from tea PPO.

In an embodiment of the present invention, where the biologically active macromolecule used in step (d) is PPO, preferably from tea plant.

In an embodiment of the present invention, where the molar ratio of acrylate polymer and 1,-carbonyldiimidazole is about 2:1.

In an embodiment of the present invention, where the immobilization of the oxidase is occurring in both forms as water soluble and in bound forms.

In an embodiment of the present invention, where the binding capacity of the PPO is about 11.5 mg/1 g of matrix.

In an embodiment of the present invention, where the conversion of tea substrate to theaflavins is 90 percent.

The present invention provides polymer: target molecule adducts which are indirectly covalently linked from the activating group on the polymer. The coupling step may be performed in an aqueous medium and occurs rapidly thus minimizing damage to labile target species.

The invention therefore provides a process for producing an adduct of polymer and a target material which comprises the following steps:

(a) reacting carbonyldiimidazole with the polymer of general formula (I)

$$-\text{[CH}_2-\text{C(COOH)]}_x-\text{[CH}_2-\text{C(C}_6\text{H}_4)-\text{CH}-\text{CH}_2\text{]}_y- \text{ or}$$

$$-\text{[CH}_2-\text{C(CO}_2\text{C}_2\text{H}_5)\text{]}_y-$$

(with R substituent)

Where R=H, $CH_3$ or $C_2H_5$ and x and y could be any number depending on the polymer composition.

(b) forming an activated imidazole polymer of formula (II)

$$-\text{[CH}_2-\text{CH]}_x-$$
$$\text{C}(=O)-\text{[N}\diagup\diagdown\text{N]}_z$$

(II)

Here x and z are positive numbers (c) reacting the activated polymer (II) with the target moiety and recovering the adduct of the polymer and the target material (III)

$$-\text{[CH}_2-\text{CH]}_x-$$
$$\text{C}(=O)-\text{[NH-E]}_z$$

(III)

here NH-E is a target moiety (Enzymes)

In which process:
(i) the polymer of formula (I) obtained as water insoluble dried powder having particle size in the range of 50 to 200 microns or obtained as a thin film of thickness of 0.15 to 0.3 mm.

(ii) the polymer formed in step (i) is reacted with CDI (1,1-carbonyldiimidazole) in dichloromethane taken in a flat bottomed flask maintained at 4° C. in an ice bath and the whole mixture was stirred at room temperature (20° C.) on a magnetic stirrer for half an hour, during the process of-which the imidazole activated polymer product so formed, was (iii) filtered through Buchner funnel using Whatman filter paper No.2 and the activated polymer resin then washed with 25 ml dichloromethane and dried under vacuum.

(iv) the imidazole-activated polymer of formula (II) so produced was recovered dry and stored at 4° C. under fridge till further use.

The product of step (iv) was then used directly in step (c) or stored so as to avoid hydrolysis prior to use in step (c) and (v) the reaction in step (c) of the activated polymer with the target material was conducted in a non-denaturing medium preferably in phosphate buffer of pH 6.2 at non-denaturing temperature with respect to the target material.

The polymer of formula (I) used in the present invention is all based on known and readily available polymer. The polymer can be used directly as available commercially or can be synthesized in the laboratory using known techniques.

It is worth mentioning here that, since the polymer and/or the target materials may be multivalent, it is possible by the process of the invention to produce a variety of polymers: target structures.

In general, the target moieties are likely to have more than one reactive group, which will then react, with the activated polymer and the possibility of forming complex structures must therefore, always be considered.

The present invention, therefore, provides the following particular embodiments of the process:

1. A process as described above comprising, in step (c), reacting in predetermined molar ratio and predetermined molar concentrations, carbonyldiimidazole activated polymer with target moiety so as to produce a 1:1 adduct of polymer and target moiety to produce polymer: target adduct and recovering the adduct in accordance with step (d).

2. A process as described above comprising, in step (c), reacting in predetermined molar ratio and molar concentrations, activated polymer with a target moiety having more than one reactive groups so as to form an adduct of the polymer and target in which preselected proportions of the reactive groups have been reacted and linked to polymer molecules especially with macromolecule targets. The preselected proportion may be, for instances from 1-100% preferably from 10-90% e.g. 10, 20, 30, 40, 50, 60, 70, 80, or 90%.

3. A process as described above comprising, in step (c), reacting in predetermined molar ratio and predetermined molar concentrations, carbonyldiimidazole activated polymer with target moiety so as to form adduct of polymer and target having two or more covalent bonds between the polymer and target moieties and then recovering the adduct in accordance with step (d).

The reagent used in the process of invention will be described as follows:

The reagent 1,1-carbonyldiimidazole used in step (a) is the compound having following structure:

The acrylate polymer of formula (I) used in the present invention are all based on known and readily available polymers which generally contain reactive groups especially carboxylate to carbonylating reagents especially carbonyldiimidazole used in the present invention. The polymer of formula (I) are acrylates of varying chain length having functional groups to carbonylating reagents such as amide, hydroxyls or carboxyls, the preferred one being carboxyls.

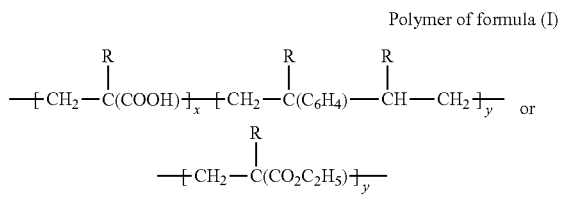

Polymer of formula (I)

Typically the polymer is nontoxic, water in-soluble in vivo and in vitro having molecular weight ranging 30,000 to 1,00,000 or more. The polymer own inherent hydrophobicity is also important in getting the reaction product of polymer target adduct with suitable substrate released to medium. The reactive carboxyl groups are terminal carboxyl groups depending upon the selected polymer, such groups may already be available for reaction or it may be necessary to introduce such groups by conventional techniques in preliminary steps. Generally the carboxyl groups are bonds to carbon atom of the polymers. The carboxyl groups must be capable of reacting to the carbonylating reagent (1,1-carbonyldiimidazole). The carboxyl groups are such that these ultimately permit formation of the desired covalent link between the polymer and the target. Such carboxyl reacts with 1,1-carbonyldiimidazole to form activated imidazole moieties.

Production of the polymer for use in the process of the present invention may be achieved by conventional techniques although most materials will be obtained commercially, possibly then modifying to introduce the desired carboxyl reactive group functionality.

The preferred polymer for use in accordance with the present invention is when x, y is large enough for the molecular weight ranging from 30,000 to 1,00,000 Daltons.

Target Materials

Suitable target materials to which polymer can be attached in accordance with the present invention are all materials having biological activity preferably plant oxidases of both soluble and bound form especially tea polyphenol oxidase (PPO) which are useful, for instance, in making products of pharmaceutical and neutraceutical importance. These are containing at least one reactive group (hereinafter referred to as group ("N") containing an atom capable of mounting a nucleophilic attack on the carbon atom of the polymer adjacent to the imidazole group. Examples of the reactive group include primary and secondary amino groups, as well as aromatic hydroxyl groups.

The target molecules may also be part of larger molecular structure. It will be appreciated that where the target molecules are part of such structure there will generally be many target molecules in each structure.

It is surmised from inventor's investigation that much of the loss of biological activity frequently observed with prior polymer coupling methods, is due to inappropriate coupling reactions, coupling conditions and/or contaminating toxic material reducing responses in bioassay and more importantly of inappropriate choice of polymer matrix without having suitable hydrophobicity in it causing product binding during reaction with suitable substrates in subsequent matrix poisoning and loss of biological activity.

The present process provides a means of generating adduct of polymer and target with highly conserved biological activity for the majority of molecules, or even enhanced biological activity.

The Process

The process of the present invention relies upon conducting steps (a) and step (b) in accordance with certain constraints as defined above in particular step (a) must be conducted using steps (i) to (iii) as described above.

The activated polymer is used directly following it's production in accordance with step (a) as this affords the minimum opportunity for degradation leading to formation of active matrix species which will interfere with subsequent reaction. If the product is to be stored prior to use, for instance, when formed in bulk for use in smaller quantities at a later date, it must be stored so as to avoid hydrolysis i.e. at a temperature sufficiently low to avoid thermal degradation preferably at 4° C. in the fridge.

The reaction of the activated polymer with the target material in step (c) takes place in a non-denaturing medium, for many biological materials particularly enzymes, this will necessarily be an aqueous medium preferably buffers of suitable nature and pH and ionic strength. Selection of pH, salt concentration, protein concentration and other requirements for stability will be determined on a case-to-case basis. Those skilled in the art will have no difficulty with this.

It is preferred that the reagents for step (a) are mixed at a temperature preferably at 4° C.

The reaction mixture is allowed to come at an ambient temperature of 20° C.

When the polymer I has more —OH groups instead of —COOH, the activated polymer target adduct generated from such polymers will bind to product in subsequent reactions with suitable substrates and eventually poison the matrix and partial or complete loss of biological activity is observed.

Most preferred molar ratio of polymer: 1,1-carbonyldiimidazole is 2:1.

The Product

Figure 2:
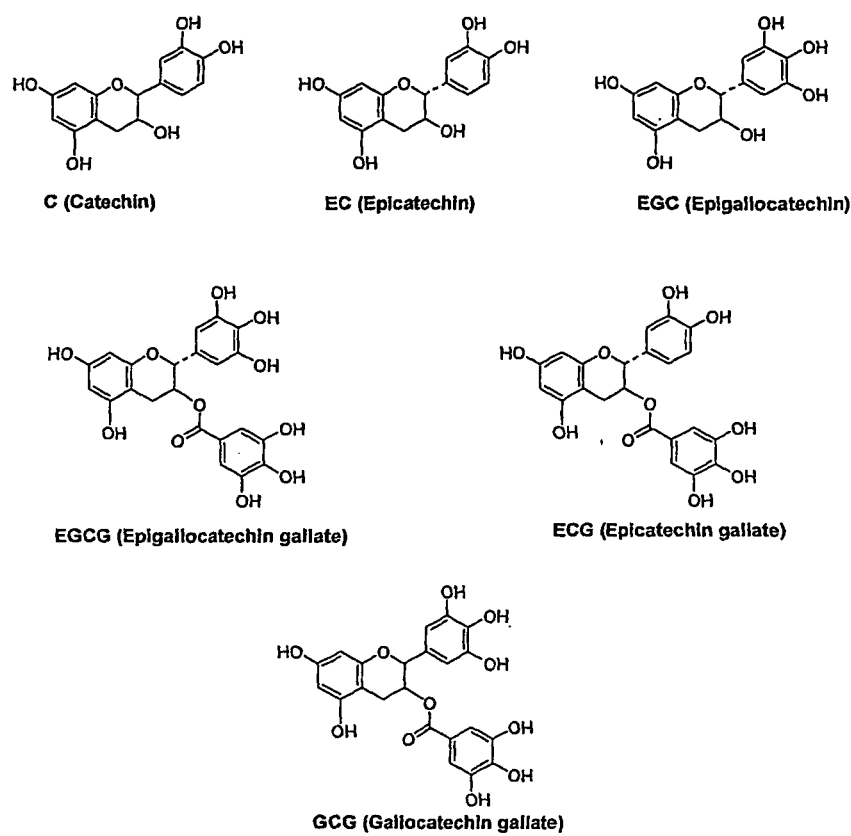
Figure 3:
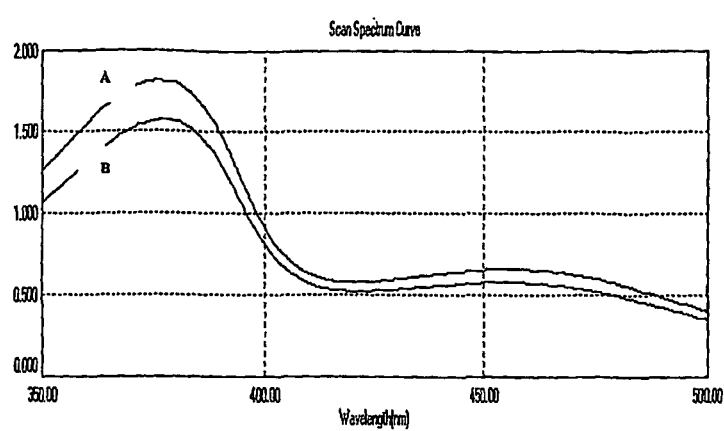
Figure 4:
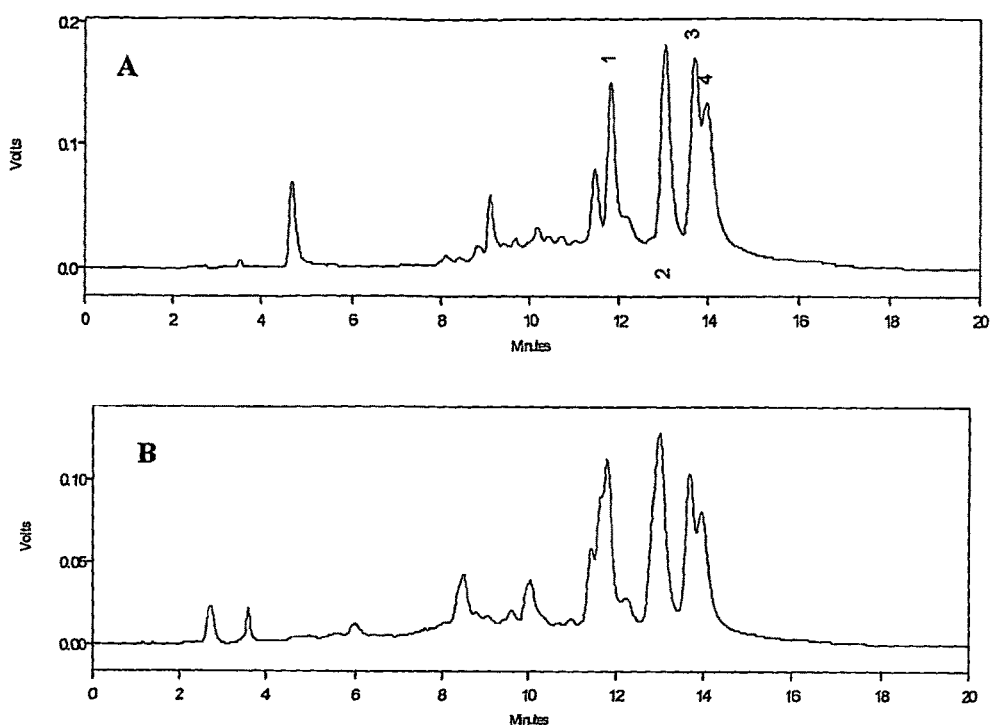

The invention also extends to such products for use in therapeutic and diagnostic methods of treatment of the human or animal bodies and to the use of such products in the manufacture of medicaments for use in therapeutic and diagnostic methods of treatment of the human or animal body and to pharmaceutical composition comprising products of the invention together with pharmaceutically acceptable diluents and carrier, the preferred product being theaflavins as identified by spectrophotometric and HPLC analysis and compared with reference standard (Sigma) which shows absorbance at 380 nm and at 460 nm as shown in FIGS. 3 & 4 (Reference may be made to Coxon, D. T.; Holmes. A; Ollis, W. D. and Vora, V. C (1970), Tetrahedron Letters, 5237-40). Typical of theaflavins as shown in FIG. 2 representing the comparative spectrophotometric analysis of theaflavins as extracted from black tea and as produced from the immobilized enzyme system. The product also reacts with Flavognost reagent (diphenyl boric acid ethanol amine) to produce green color. (Reference may be made to Robertson, A & Hall, M. N. (1989), Food Chemistry, 34, 51-70). as is done by natural compound thereby further identifying as being theaflavins.

The process of the present invention makes the production of the constructs such as the following, which form particular embodiment of the present invention:

Constructs where a plurality of identical target molecules are linked to a single polymer moiety; for instance a linear polymer having two or more reactive termini is linked to target molecules to enhance the biological activity thereof or a branched polymer having three or more reactive termini or a polymer having reactive pendant is linked to three or more target molecules.

Constructs wherein, the polymer moiety is linked to a target molecule at two or more positions either by reaction of both termini of a linear polymer with different sites or the target molecules or by reaction of pendant reactive groups, or the termini of a branched polymer, at two, three, or more sites on the target molecules. The product of the present invention preferably comprises any one or more of polymer target materials set out above.

Particularly preferred products of the invention are adduct of a polyacrylate especially polymethylacrylic acid or polyethylacrylic acid and their polymer in different ratio with any one or more of the target materials being oxidases in nature especially tea polyphenol oxidase being particularly preferred to generate specifically immobilized enzyme mediated product with the enzyme specific substrates the most preferred product being the theaflavins by the reaction of tea polyphenol oxidase with its substrates.

The process of the present invention enables the production of constructs such as following which form particular embodiments of the present invention:
1. Constructs where the target materials comprising preferably crude soluble PPO from tea and cross linked to activated polymer generated as in (b) in specified ratio.
2. Constructs as in (1) above wherein the target molecules are different: such as enzymes of similar nature from other sources.
3. The product of the present invention preferably comprises any one of the polymer material set out above and any one or more of the target materials preferably tea PPO set out above particularly preferred product of the present invention are the adduct of methylacrylate, ethylacrylate polymer having carboxyl group functionality, where the former being most preferred, with the target material set out above with tea PPO being most preferred.
4. Isolating the activated polymer adduct as generated in 3 and reacting with tea substrate to generate exclusively, a product theaflavins time and again without losing biological activity of polymer-target adduct.

The production of the adducts wherein target species are coupled to a multivalent polymer presents special difficulties which can be overcome by present invention. For this situation, an appropriate procedure for producing a product involves the following steps:

Target (A), soluble plant oxidases particularly soluble tea PPO, is exposed to activated polymer (imidazole-acrylate) with the specific ratio of target to polymer to fine tune coupling ratio, reaction time, and/or pH so as to completely cross link all the enzyme to polymer, separating out the target: polymer adduct, washing it with aqueous buffer for use in product formation repeatedly.

In an embodiment of the present invention the crude Tea Polyphenol Oxidase enzyme (EC1.10.3.1) herein after referred to as PPO, was extracted from tea plant parts like leaves, flowers, buds, seed bark, etc. but the preferred source being the young tea shoots comprising two leaves and attached bud, herein referred to as tea shoots. The process involves grinding of fresh tea shoots in pre-cooled (4° C.) acetone, passing the macerate through sintered glass funnel of porosity G3 and washing of all green color with fresh aliquots of chilled acetone two or three times, washing of the residue so obtained with chilled 70% acetone (acetone:water; 70/30 v/v) and finally washing the residue so obtained with chilled acetone to remove water left in the previous washings. The acetone powder so prepared was vacuum dried. During the preparation of acetone powder, washing with chilled (4° C.), 70% aqueous acetone helped in the removal of adhered phenolics and giving material free from phenolic matter which otherwise could affect solubilisation. For solubilisation of PPO, weighed amount of acetone powder so prepared, was first ground with distilled water and filtered through cotton wool plug over a funnel under mild suction so as to remove starch and unwanted soluble proteins. The material so washed was then eluted with 0.2M $Na_2SO_4$ solution which effected solubilisation of 80-90% PPO activity from the acetone powder.

In another embodiment of the present invention the tea substrate was prepared from tea shoots and tea seed barks. The fresh tea shoots/tea seed coats were first steamed for three minutes to deactivate the polyphenol oxidase enzyme and then macerated in 30% acetone taken in a beaker. The whole mixture was covered with aluminum foil and kept overnight.

The mixture was then filtered through sintered glass funnel. The residue was rejected and filtrate was partitioned with 2:1 (v/v) petroleum benzine (60-80° C. fraction) ethyl acetate mixture for three or four times. The organic layer was rejected and the aqueous layer was repeatedly extracted with ethyl acetate. The aqueous layer was rejected and the ethyl acetate layer was shaken with aliquot of water and two-volume petroleum benzine. After rejecting the organic phase, the aqueous substrate phase was spray dried.

In yet another embodiment of the present invention the adduct of polymer and target material was made according to step (a), (b) and (c) and activated solid state matrix so generated (step a-b) was made use of to crosslink/covalently bounded biologically active macromolecules (step c) especially plant oxidase, the most preferred being tea PPO to generate repeatedly in vitro oxidase mediated products, the most preferred being, exclusive Theaflavins from tea substrate with immobilized tea PPO matrix.

In still yet another embodiment of the present invention the exclusive and most preferred product, theaflavins so generated were repeatedly isolated and produced in batch operation in large amounts and in an economical manner time and again using the same solid state enzyme matrix.

The following examples are given by way of illustration and therefore should not be construed to limit the scope of the present invention.

EXAMPLE-1

The 0.3 g matrix (CDI activated acrylate based polymer resin) was suspended in 3 ml 6.2 pH phosphate buffer in a plastic beaker and to this 2.0 ml crude polyphenol oxidase enzyme extracted from tea shoots (1.66 mg×2-enzyme protein) was added; the whole mixture was incubated in an incubator shaker at 25° C. and at 100 r.p.m. for one hour; after incubation, the mixture was filtered through glass wool and the filtrate was checked for enzyme activity with tea substrate which was found devoid of any enzyme activity indicated thereby that the whole of the enzyme proteins were bound to the matrix; the matrix bound immobilized enzyme was then washed with 10 ml water and filtrate was rechecked for residual enzyme activity which was not detected in the filtrate indicated covalent bonding of the enzyme to the matrix; to the above matrix taken in a plastic beaker, 0.04 g of tea substrate dissolved in 4.0 ml water was added and then incubated in an incubator-shaker for half an hour at 37.5° C. and 100 r.p.m. and the product (Theaflavin) so formed during the course of reaction was filtered freeze dried, spray dried or solvent (ethyl acetate) extracted to obtain pure product and the matrix was washed with 15% acetone followed with water and the same procedure was repeated n numbers of times with the same immobilized enzyme system to obtain similar product without any deactivation of the enzyme system covalently bound to the matrix which has the binding capacity as 11.5-mg enzyme proteins/1.0 g of the matrix; the general reaction and mechanism is as shown below in FIG. 1(a) and FIG. 1(b) respectively.

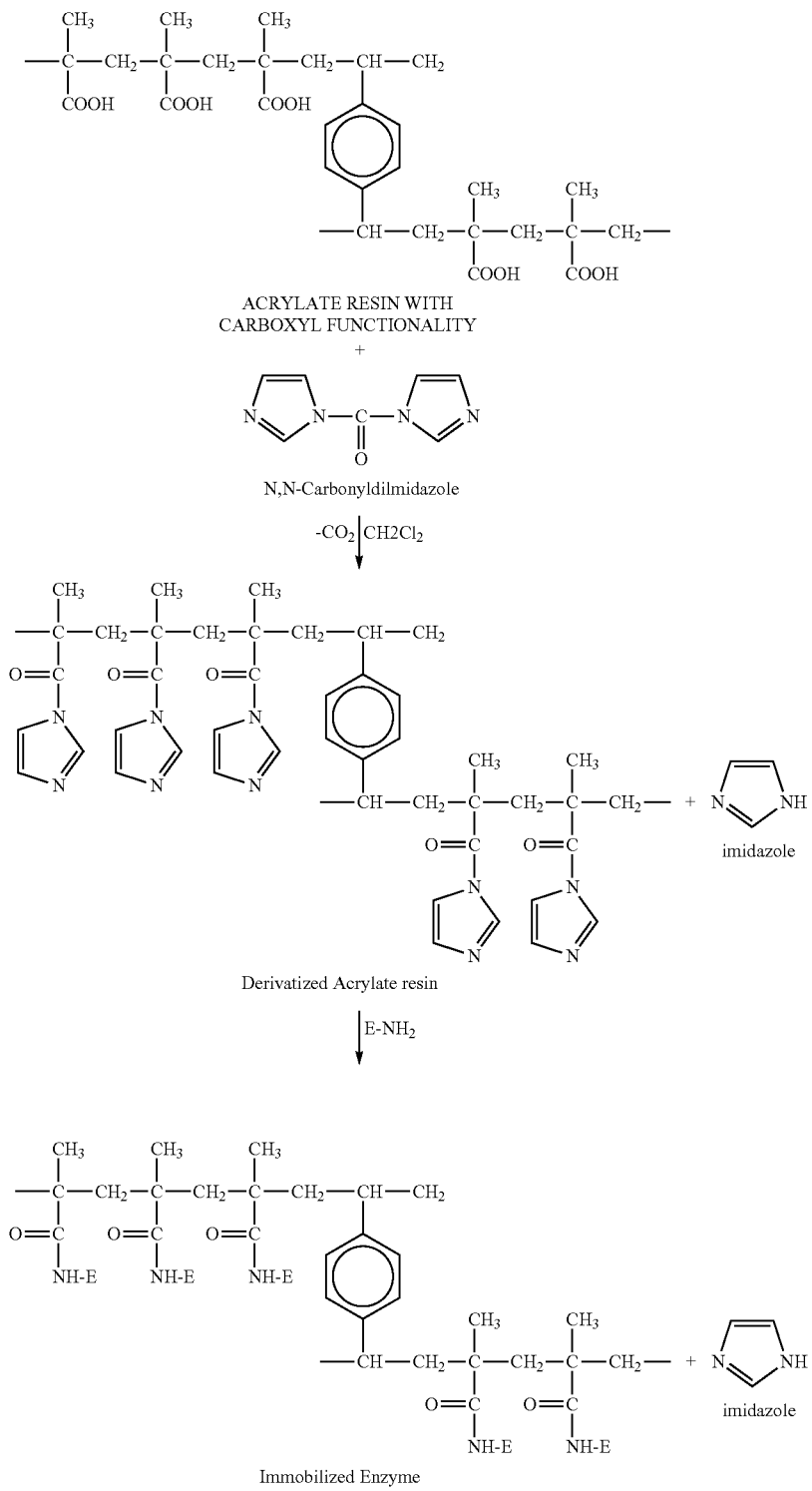

Fig.1(a) General reaction for matrix activation and Enzyme immobilization.
Fig.1(b) Reaction mechanism for matrix activation and Enzyme immobilization.

EXAMPLE-II

The 0.5 g matrix (CDI activated acrylate based polymer resin) was suspended in 5 ml 6.2 pH phosphate buffer in a plastic beaker and to this 5.0 ml crude polyphenol oxidase enzyme extracted from litchi (litchi chinensis) shoots (1.15 mg×2-enzyme protein) was added and the whole mixture was incubated in an incubator shaker at 20° C. and at 100 r.p.m. for two hours at the end of which, the mixture was filtered through glass wool, and the filtrate was checked for enzyme activity with litchi substrate which was found devoid of any enzyme activity indicated thereby that the whole enzyme proteins were bound to the matrix; the matrix bound immobilized enzyme was then washed with 10-ml water and filtrate was rechecked for residual enzyme activity which was not detected in the filtrate indicated covalent bonding of the enzyme to the matrix; the above matrix was taken in a plastic beaker to which 0.05 g litchi substrate dissolved in 5.0 ml water was added and then incubated in an incubator-shaker for half an hour at 25° C. and 100 r.p.m. and the product so formed during the course of reaction was filtered, the matrix was washed with water and the same procedure was repeated for n numbers of times to obtain similar product without any deactivation of the enzyme system covalently bound to the matrix which has the binding capacity as 11.5-mg enzyme proteins/1.0 g of the matrix; (a) the crude Polyphenol oxidase enzyme from litchi Leaves as described above in was extracted from tender Litchi leaves and the process involved preparation of acetone powder similar to Example I; the vacuum dried weighed amount of acetone powder so prepared was eluted with double distilled water, which effected solubilization of 80-90% Polyphenoloxidase activity from the acetone powder and (b) the litchi substrate as described was prepared from fresh litchi leaves similar to as for preparation of tea substrate.

The Main Advantages of the Present Invention are:
1. Utilization of acrylate based polymer resins having specialized functional groups as an efficient matrix for immobilization through cross linking/covalent bonding of biologically active macromolecules especially plant oxidases, the most preferred being tea polyphenol oxidase after derivatization with 1,1-Carbonyl diimidazole.
2. The activated polymer resin enzyme adduct as mentioned in (1) is thermally stable and exhibit "n" numbers of turnovers of tea substrates into theaflavin without any loss in activity of enzyme at room temperature (20° C.) or elevated temperatures upto 60° C.
3. By way of utilization of polymer resins as in (1) as an immobilization matrix after the derivatization with 1,1-Carbonyl diimidazole helps in the exclusive and total conversion of enzyme substrate the most preferred being the tea substrate into Theaflavins.
4. The activated polymer resin as in (2) showed stronger binding with biologically active macromolecules especially plant oxidases both of soluble and bound forms; the most preferred being tea polyphenol oxidase.

We claim:
1. A process for converting a tea substrate to theaflavins comprising the steps:
   a) incubating a mixture of a tea substrate dissolved in water and a solid state matrix, the solid state matrix being of formula III,

Formula III wherein X is up to about 30, Z is one per carboxyl group in a polymer chain length: E is polyphenol oxidase enzyme (PPO), at a temperature ranging between 25° C. to 37.5° C. for a period ranging between 30 minutes to 2 hour, and
   b) separating the matrix from the mixture to obtain filtrate containing the product theaflavins and recycling the matrix after washing with acetone followed by water, wherein the PPO used is selected from an enzyme obtained from tea or litchi.

2. The process as claimed in claim 1, wherein the matrix is stable at a temperature up to 60 deg. C.

3. The process as claimed in claim 1, wherein the matrix immobilized with PPO is useful for the conversion of substrate selected from the same plant to obtain the corresponding products.

4. The process as claimed in claim 1, wherein the polyphenol oxidase used is tea PPO, useful for the conversion of the tea substrates to theaflavins.

5. The process as claimed in claim 1, wherein the PPO used is litchi PPO, useful for the conversion of litchi substrate to the orange colored product derived from polymerized quinones from litchi substrate.

6. The process as claimed in claim 1, wherein the matrix is effectively used for at least 50 numbers of turnover to convert the tea substrate to theaflavins without loss of enzyme activity.

7. The process as claimed in claim 1, wherein the polymer used is selected from a resin consisting of methylacrylate polymer, ethylacrylate polymer or butylacrylate polymer.

8. The process as claimed in claim 1, wherein the polymer used is methylacrylate.

* * * * *